(12) United States Patent
Sliwa et al.

(10) Patent No.: US 12,220,157 B2
(45) Date of Patent: Feb. 11, 2025

(54) PULMONARY ANTRUM RADIAL-LINEAR ABLATION DEVICES

(71) Applicant: St. Jude Medical, Cardiology Division, Inc., St. Paul, MN (US)

(72) Inventors: John W. Sliwa, San Jose, CA (US); Stephen A. Morse, Menlo Park, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 649 days.

(21) Appl. No.: 16/619,784

(22) PCT Filed: Jun. 5, 2018

(86) PCT No.: PCT/US2018/036141
§ 371 (c)(1),
(2) Date: Dec. 5, 2019

(87) PCT Pub. No.: WO2018/226752
PCT Pub. Date: Dec. 13, 2018

(65) Prior Publication Data
US 2020/0129218 A1    Apr. 30, 2020

Related U.S. Application Data

(60) Provisional application No. 62/515,501, filed on Jun. 5, 2017.

(51) Int. Cl.
*A61B 18/14*    (2006.01)
*A61B 18/00*    (2006.01)
(Continued)

(52) U.S. Cl.
CPC .............. *A61B 18/00* (2013.01); *A61N 7/022* (2013.01); *A61B 2017/320069* (2017.08);
(Continued)

(58) Field of Classification Search
CPC ... A61B 18/02; A61B 18/082; A61B 18/1206; A61B 18/1492; A61B 2018/00005;
(Continued)

(56) References Cited

U.S. PATENT DOCUMENTS 5,277,201 A * 1/1994 Stern ..................... A61N 1/06
606/41
5,569,241 A * 10/1996 Edwards ........... A61M 16/0481
606/41
(Continued)

FOREIGN PATENT DOCUMENTS

JP    2016-185296 A    10/2016
WO   2018/226751 A1    6/2018

*Primary Examiner* — Michael F Peffley
(74) *Attorney, Agent, or Firm* — Armstrong Teasdale LLP

(57) ABSTRACT

Devices and methods for creating radial-linear lesions in pulmonary vein antral tissue are disclosed. In an embodiment, a device includes an elongate shaft structure with a distal tip ablation region including a spline and an ablation element slidably coupled to the spline. The ablation element includes at least one of an ultrasound emitter, a high frequency ultrasound emitter, a laser, a radiofrequency electrode, a virtual radiofrequency electrode, or a cryogenic source. A backing balloon may be configured to push or pull the spline and the ablation element toward or against the pulmonary vein antral tissue. In an embodiment, the distal tip ablation region includes a splineless cryoballoon with at least one thermally conductive region.

11 Claims, 5 Drawing Sheets

(51) Int. Cl.
*A61N 7/02* (2006.01)
*A61B 17/32* (2006.01)
*A61B 18/02* (2006.01)
*A61B 18/08* (2006.01)
*A61B 18/12* (2006.01)
*A61B 18/24* (2006.01)

(52) U.S. Cl.
CPC ............... *A61B 2018/00005* (2013.01); *A61B 2018/00095* (2013.01); *A61B 2018/0022* (2013.01); *A61B 2018/00238* (2013.01); *A61B 2018/00255* (2013.01); *A61B 2018/00285* (2013.01); *A61B 2018/00375* (2013.01); *A61B 2018/00577* (2013.01); *A61B 2018/00791* (2013.01); *A61B 2018/0212* (2013.01); *A61B 18/082* (2013.01); *A61B 18/1206* (2013.01); *A61B 2018/1472* (2013.01); *A61B 18/1492* (2013.01); *A61B 18/24* (2013.01)

(58) Field of Classification Search
CPC ........... A61B 2018/00095; A61B 2018/00214; A61B 2018/0022; A61B 2018/00238; A61B 2018/00255; A61B 2018/00285; A61B 2018/00375; A61B 2018/00577; A61B 2018/00791; A61B 2018/0212; A61B 2018/1472

See application file for complete search history.

(56) References Cited

U.S. PATENT DOCUMENTS

| | | | | |
|---|---|---|---|---|
| 5,779,698 | A * | 7/1998 | Clayman | A61M 25/104 607/101 |
| 5,860,974 | A * | 1/1999 | Abele | A61B 8/12 606/41 |
| 6,036,689 | A * | 3/2000 | Tu | A61B 18/1492 604/103.08 |
| 6,071,278 | A * | 6/2000 | Panescu | A61B 18/1492 606/41 |
| 6,142,993 | A * | 11/2000 | Whayne | A61B 18/1492 606/41 |
| 6,500,174 | B1 * | 12/2002 | Maguire | A61B 18/1492 606/49 |
| 7,736,362 | B2 * | 6/2010 | Eberl | A61M 25/1029 606/49 |
| 8,617,150 | B2 * | 12/2013 | Tsoref | A61N 7/00 606/41 |
| 8,845,632 | B2 * | 9/2014 | Qin | A61B 34/25 606/41 |
| 9,237,925 | B2 * | 1/2016 | Fischell | A61B 90/39 |
| 2002/0087151 | A1 | 7/2002 | Mody et al. | |
| 2008/0243111 | A1 | 10/2008 | Gammie et al. | |
| 2015/0045789 | A1 * | 2/2015 | Edwards | A61B 18/18 606/41 |
| 2015/0157402 | A1 | 6/2015 | Kunis et al. | |
| 2015/0374436 | A1 | 12/2015 | Subramaniam et al. | |

* cited by examiner

PULMONARY ANTRUM RADIAL-LINEAR ABLATION DEVICES

CROSS-REFERENCE TO RELATED APPLICATIONS

This application is a National Stage Entry of International application no. PCT/US2018/036141, filed 5 June 2018 (the '141 application), and published under International publication no. WO 2018/226752 on 13 December 2018. This application claims priority to Provisional patent application No. 62/515,501, filed 5 June 2017 (the '501 application). The '141 application and the '501 application are all hereby incorporated by reference as though fully set forth herein.

BACKGROUND a. Field

This disclosure relates to an ablation catheter configured to form radial-linear lesions at the pulmonary vein antrum region in the left atrium of the heart.

b. Background Art

Electrophysiology (EP) catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrio-ventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

Foci of atrial fibrillation often originate within the pulmonary veins. A procedure called pulmonary vein isolation (PVI) has been the cornerstone for delivery of ablation therapy to regions surrounding the pulmonary vein ostia in the left atrium. PVI involves forming circumferential "ring-type" lesions around the pulmonary vein ostia. A newer and potentially more effective method of treating atrial fibrillation is pulmonary vein antrum radial-linear (PAR) ablation. PAR ablation involves the creation of radial-linear lesions, rather than circumferential lesions, around the pulmonary vein ostia and/or antrum.

BRIEF SUMMARY

In an embodiment, a pulmonary vein antrum radial-linear (PAR) ablation catheter comprises: an elongate shaft structure comprising a proximal end and a distal end, the distal end including a distal tip ablation region comprising: a spline; and an ablation element slidably coupled to the spline; wherein the ablation element is configured to form radial-linear lesions in or near pulmonary vein antral tissue.

In another embodiment, a PAR ablation catheter comprises: an elongate shaft structure comprising a proximal end and a distal end; wherein the distal end comprises a distal tip ablation region including an energy transfer balloon; and wherein the energy transfer balloon comprises at least one thermally conductive ablating region configured to form radial-linear lesions in or near pulmonary vein antral tissue.

In another embodiment, a PAR ablation catheter comprises: an elongate shaft structure comprising a proximal end and a distal end, the distal end including a distal tip ablation region comprising: a deployable spline; and an ablation element coupled to the spline; wherein the ablation element is configured to form radial-linear lesions in or near pulmonary vein antral tissue.

DETAILED DESCRIPTION

Figure 1:
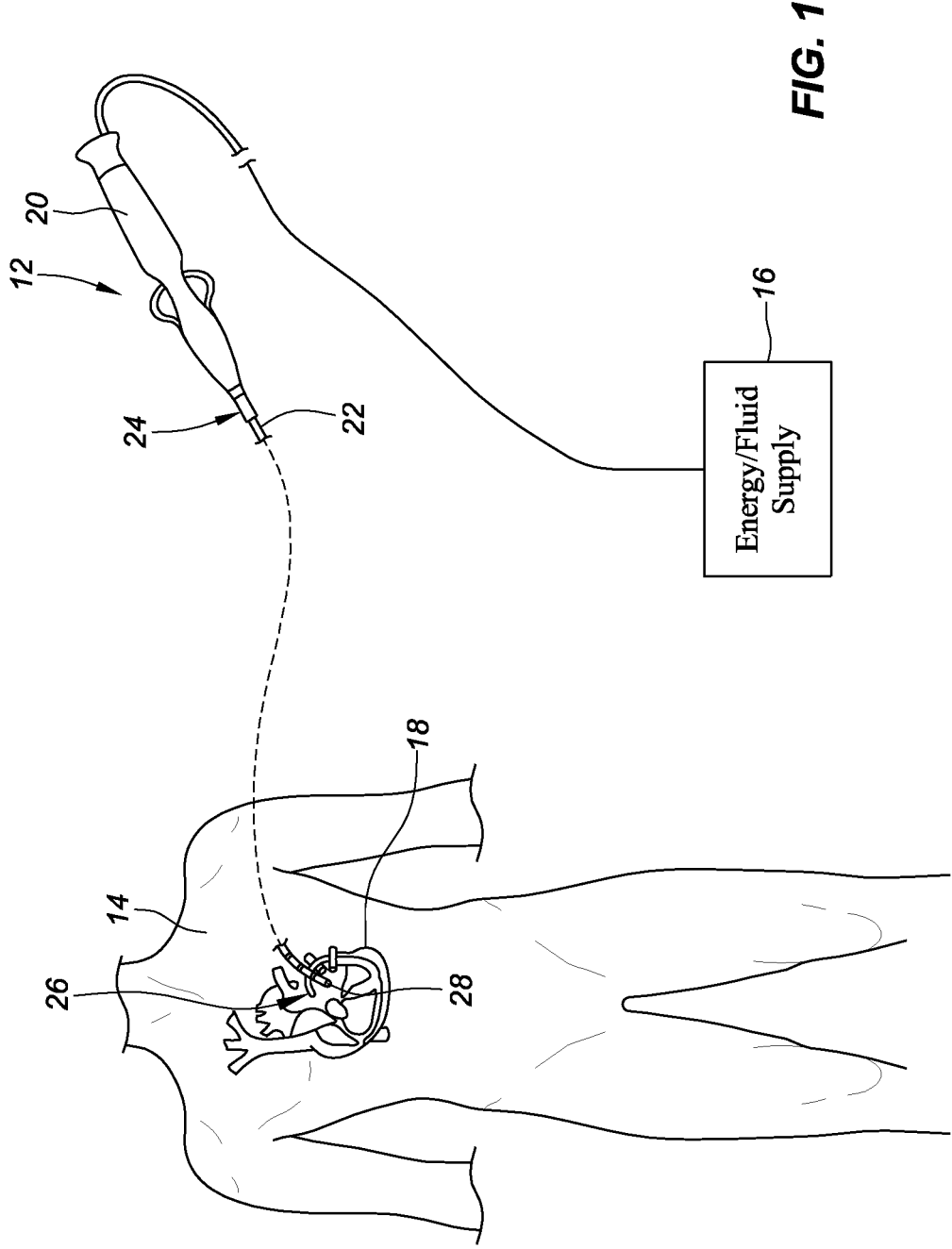
FIG. 1 is a schematic view depicting an embodiment of a catheter in accordance with the present disclosure.

FIG. 1 is a schematic view depicting a catheter 12 for use in a patient's body 14 and connected to an energy/fluid supply 16 (e.g., a radiofrequency (RF) ablation generator, a coolant supply) according to the present disclosure. In an embodiment, the catheter 12 may be an ablation catheter. The catheter 12 can be configured to be inserted into the patient's heart 18. The catheter 12 may include a handle 20 and a shaft 22 having a proximal end portion 24, a distal end portion 26, and a tip portion 28 disposed at the distal end portion 26 of the shaft 22. The catheter 12 may further include other conventional components such as, for example and without limitation, a temperature sensor, a position sensor, additional sensors or electrodes, and corresponding conductors or leads.

The shaft 22 can be an elongate, tubular, flexible member configured for movement within the body 14. The tip portion 28 of the shaft 22 supports, for example and without limitation, sensors and/or electrodes mounted thereon. The tip portion 28 may include ablation elements (e.g., ablation tip electrodes for delivering RF ablative energy) or other energy transfer elements (for example, but not limited to, ultrasound transducers, lasers, chemical ablation sources, cryoablation sources, and/or heat ablation sources) as further described in commonly owned U.S. Provisional Patent Application No. 62/515,500, which is hereby incorporated by reference in its entirety as though fully set forth herein.

The shaft 22 may also permit transport, delivery, and/or removal of fluids (including irrigation fluids, cryogenic ablation fluids, and bodily fluids), medicines, and/or surgical tools or instruments.

Figure 2:
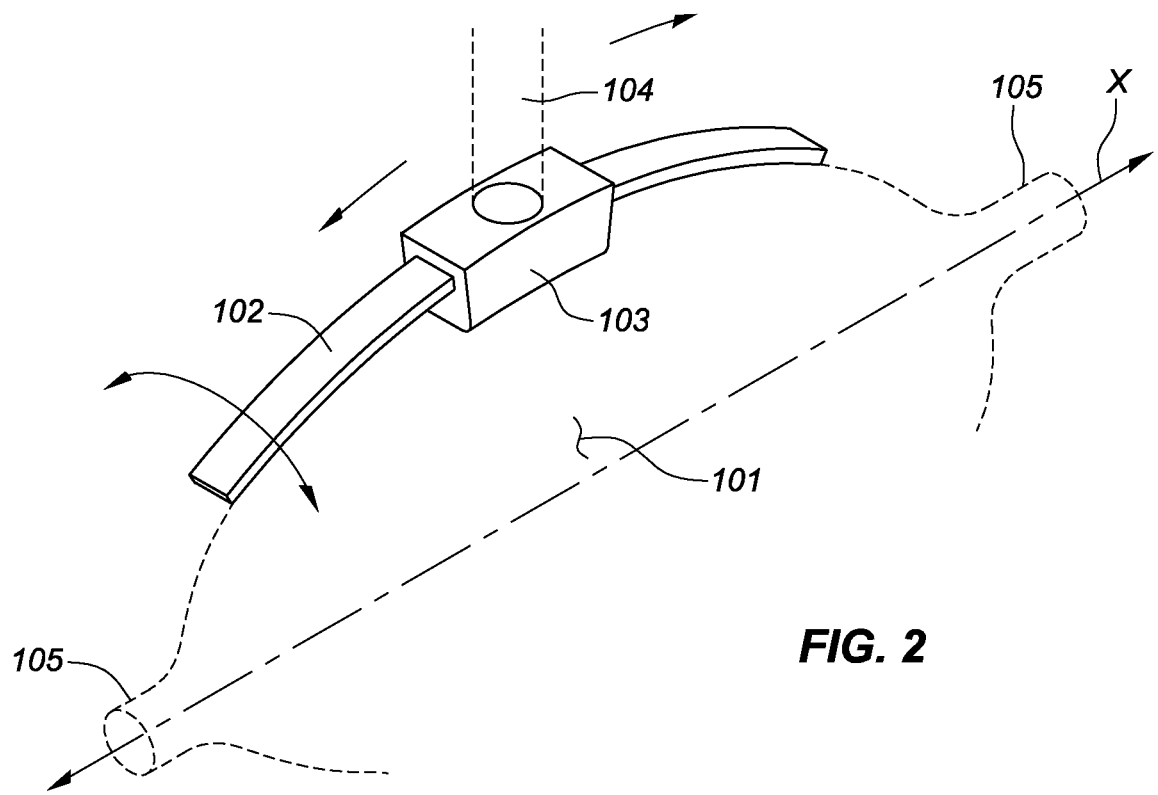
FIG. 2 is a schematic view depicting an embodiment of a PAR ablation device including a spline and a slidable therapy element.

FIG. 2 is a schematic view of a portion of a pulmonary vein antrum radial-linear (PAR) ablation device forming the distal tip portion of an ablation catheter, such as the catheter 12 described above with respect to FIG. 1. In general, "radial-linear" lesions refer to linear lesions that radiate out from the pulmonary vein ostium/antrum toward the areas surrounding the pulmonary vein or the junction between the pulmonary vein and the left atrium. A backing balloon 101, shown in phantom, can be used to deform a spline 102 against a pulmonary vein ostium and/or antrum. Although a single spline 102 is shown here, the PAR ablation device may include a plurality of splines. An ablation or energy transfer element (referred to hereinafter as "ablation element") 103 is mounted upon the spline 102. The ablation element 103 may be an RF electrode, for example, if the ablation element 103 directly contacts tissue or operates through a saline porous balloon. In another embodiment, the ablation element 103 may be a high-frequency ultrasound (HIFU) emitter with a beam 104 as shown. The beam 104 may travel through a balloon in some examples. In other embodiments, the ablation element 103 may be a laser, a virtual RF electrode, or a source of cryogen (e.g., an evaporating phase-change cryogen or a precooled liquid cryogen).

The ablation element 103 can slide along the spline 102 such that PAR lesions are formed in accordance with the PAR ablation procedure. As few as two to four PAR lesions may be formed about a pulmonary vein ostium/antrum. As shown in FIG. 2, the backing balloon 101 has necked-down regions 105. The spline 102 may not necessarily extend all the way to the proximal or distal/proximal necked-down regions 105. In an embodiment, the spline 102 may extend from the equator of the balloon 101 to the end of the distal necked-down region 105. The spline 102 may be rotated about an axis, such as a longitudinal axis of the catheter X, so that a particular angular orientation or lesion may be chosen. In embodiments with multiple spines, one or more of the splines may be rotatable about the axis X.

Figure 3:
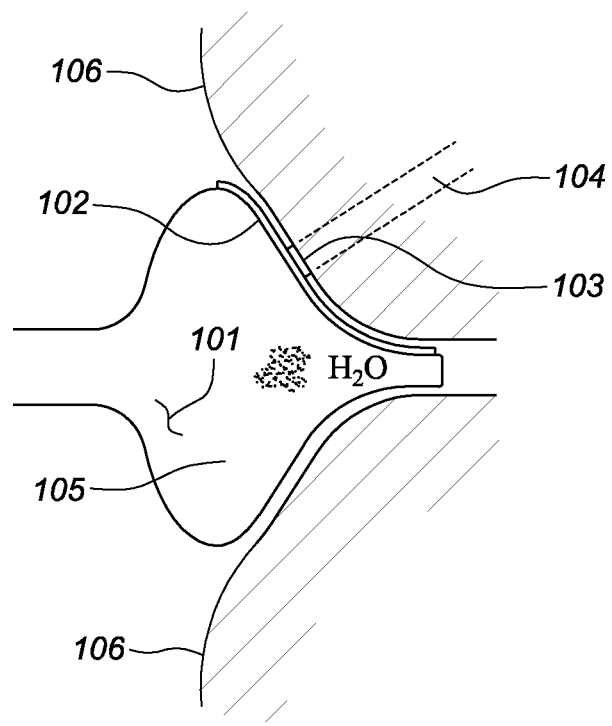
FIG. 3 is a schematic view depicting another embodiment of a PAR ablation device including a spline and a slidable therapy element.

FIG. 3 is a schematic view depicting a PAR ablation device similar to that shown in FIG. 2. In FIG. 3, however, the backing balloon 101 has been shaped to push the spline 102 and the ablation element 103 against antrum tissue 106. It should be noted that the inflatable backer balloon 101 is one option for tissue-placement of the spline 102. Alternatively (not shown), a spring mechanism or a spring-like spline can be used to cause intimate juxtaposition of the spline 102 to the antrum tissue 106. In some embodiments, the backing balloon 101 may also (or instead) provide blood flow obstruction (e.g., to minimize blood cooling effects), surface temperature control, or a saline path for HIFU, laser light, or RF to pass through before it penetrates the antrum tissue 106. As such, the spline 102 and ablation element 103 do not necessarily have to intimately contact the antrum tissue 106. In another embodiment, a second balloon may be disposed between the spline 102/ablation element 103 and the antrum tissue 106, thus requiring the ablating energy to pass through the second balloon.

In FIGS. 2 and 3, the ablation element 103 may be driven to slide upon the spline 102 in any of several ways. For example, the ablation element 103 may be driven to slide upon the spine 102 via a push or pull wire. The ablation element 103 may also be driven to slide upon the spline 102 via a push or pull wire in a first direction and a return spring in a second direction. In this example, the push or pull wire may have a power lead for the ablation element 103.

Figure 4:
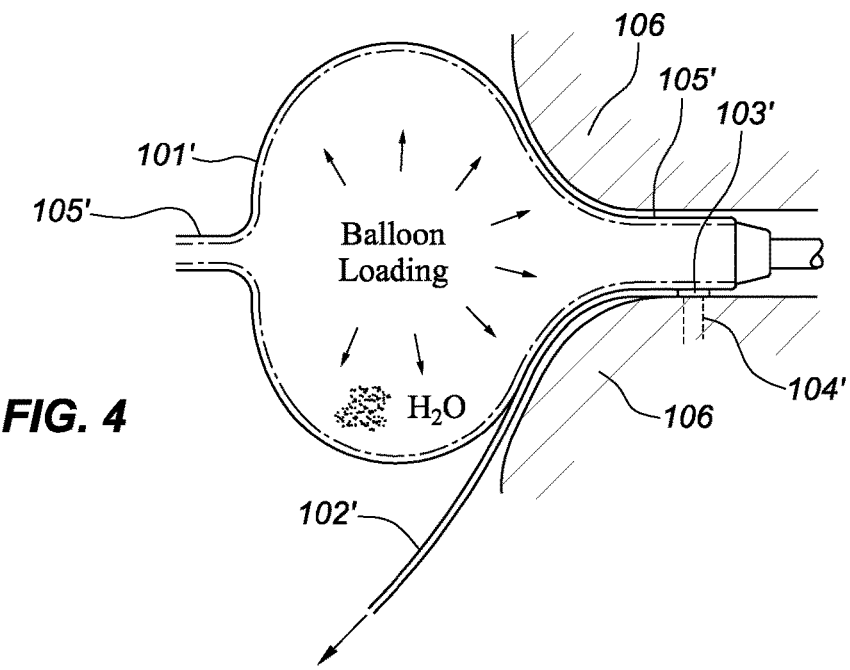
FIG. 4 is a schematic view depicting an embodiment of a PAR ablation device including a spline and a fixed or slidable therapy element.

FIG. 4 is a schematic depiction of another embodiment of a PAR ablation device. In this embodiment, a spline 102' is placed in the antrum tissue 106 and a backing or loading balloon 101' presses the spline 102', along with its ablation element 103', against the antrum tissue 106. As with ablation element 103 described above with respect to FIGS. 2 and 3, the ablation element 103' may be an RF electrode, HIFU, or a laser. In this embodiment, the spline 102' does not necessarily have to be part of a spline basket. Further, the ablation element 103' can be configured to scan along the antrum tissue 106 in one of several ways. For example, the ablation element 103' can be mounted in a non-sliding fixed position on the spline 102', and the spline 102' and the ablation element 103' can then be simply pushed, pulled, or dragged while the balloon 101' maintains reasonable tissue contact and/or proximity of the ablation element 103' to the antrum tissue 106. In another example, the ablation element 103' can be mounted in a sliding manner upon the spline 102', similar to the ablation element 103 and the spline 102 described above with respect to FIGS. 2 and 3.

FIGS. 5A-D are schematic depictions of another embodiment of a PAR ablation device involving a cryoballoon 101". The cryoballoon 101" shown in FIG. 5A can be filled with coolant, cryogen, or cryogenic fluid (cryofluid). The cryoballoon 101" includes a thermally-insulating balloon surface 1A and axial necked-down regions 105". The cryoballoon 101" can ablate linear lesions corresponding to grooved regions 1B on the balloon surface 1A. A balloon with a desired pattern of grooved regions 1B can be preselected according to pre-surgical imaging of a patient's pulmonary vein antral region, for example. Alternatively, a desired pattern of grooved regions 1B can be formed in a balloon upon use.

Figure 5A:
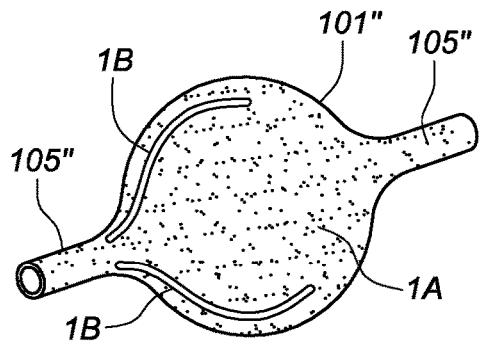
FIGS. 5A-5D are schematic views depicting an embodiment of a PAR ablation device including a splineless cryoballoon.
Figure 5B:
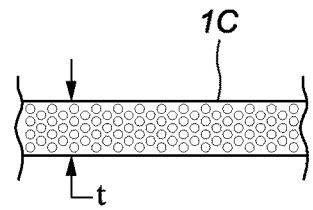
Figure 5C:
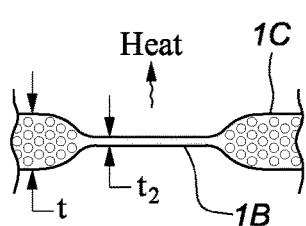
Figure 5D:
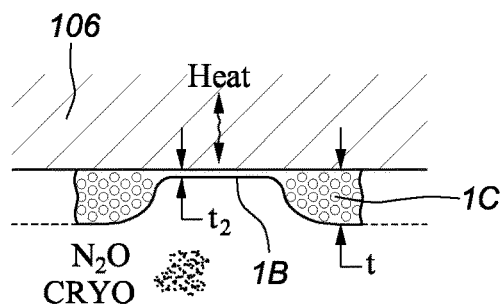

As shown in FIG. 5B, the cryoballoon 101" is fabricated from a porous, yet impermeable, polymeric film 1C of thickness t (e.g., up to several millimeters). As further shown in FIG. 5C, the porous polymeric film 1C can be thermally compressed or fused into a very thin, pore-free state (with a thickness $t_2$) that forms the grooved regions 1B in the balloon surface 1A. As a result of this thermal compression, the grooved regions 1B are more thermally conductive than the non-grooved balloon surface 1A. In this manner, cryofluid evaporation from the grooved regions 1B (or non-evaporating cold cryofluid within regions 1B of the cryoballoon 101") can selectively freeze the antrum tissue 106 adjacent to the grooved regions 1B, as shown in FIG. 5D. Although some cooling may take place through the porous regions 1C, a majority of the cooling will take place at the grooved regions 1B. Furthermore, a much greater percentage of the cooling capacity of the total surface area of the cryoballoon 101" will be attributed to the grooved regions 1B rather than being uniformly distributed (e.g., as for current circular-lesion pulmonary vein cryoballoons). In some embodiments, it may be preferable to have the grooved regions 1B face inward such that the surface of the cryoballoon 101" in those regions comes into direct contact with the antrum tissue 106, as shown in FIG. 5D.

In an alternative embodiment, the cryoballoon 101" can be fabricated from a non-porous polymeric material, and the non-ablating regions can be rendered porous in order to decrease their thermal conductivity and prevent cyroablation.

Figure 6A:
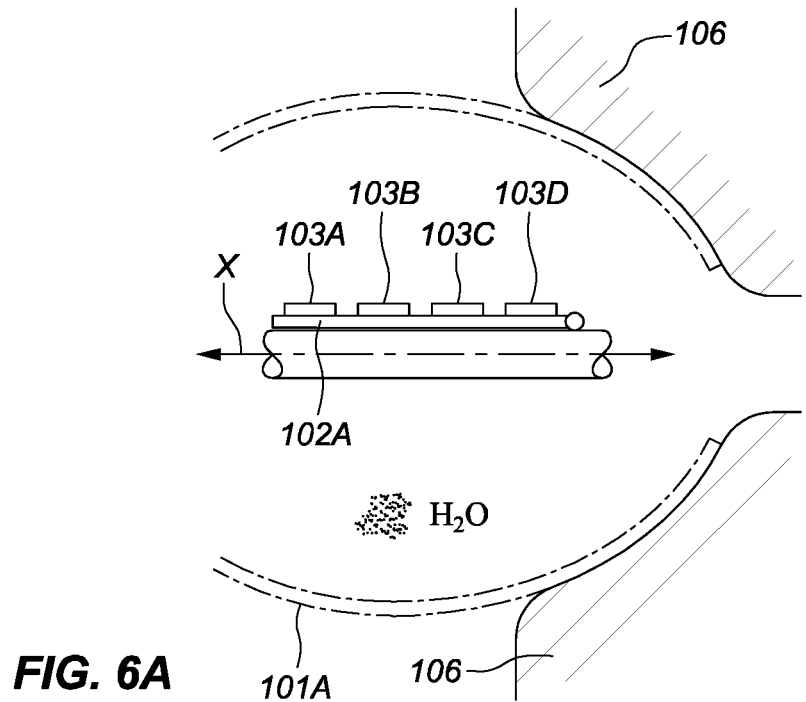
FIGS. 6A and 6B are schematic views depicting an embodiment of a PAR ablation device including a tiltable spline and therapy element.
Figure 6B:
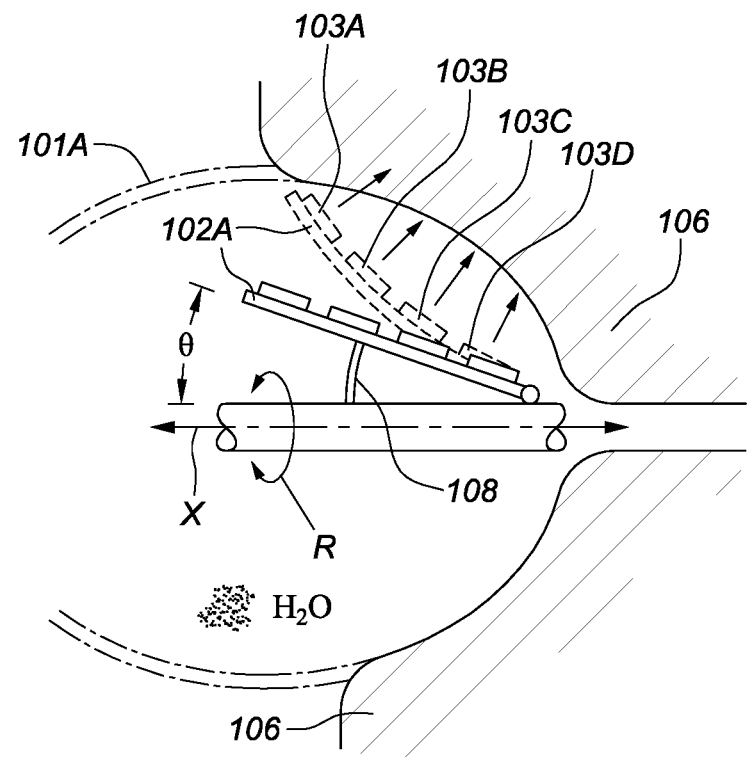

FIGS. 6A and 6B are schematic depictions of another embodiment of a PAR ablation device involving a balloon 101A. In this embodiment, ablation elements 103A, 103B, 103C, and 103D (which may be RF, HIFU, or laser elements, as with elements 103 and 103' described above with respect to FIGS. 2-4) are fixedly mounted to a spline 102A. FIG. 6A illustrates the ablation elements 103A-D in their pre-actuation state, while FIG. 6B depicts the ablation elements 103A-D once actuation has begun. As shown in FIG. 6B, the spline 102A and fixed ablation elements can be angled, tilted, or articulated through an angle θ—via an actuator 108, for example—to better face the antrum tissue 106. The spline 102A may also be rotatable in a direction R about the catheter axis X.

Figure 7:
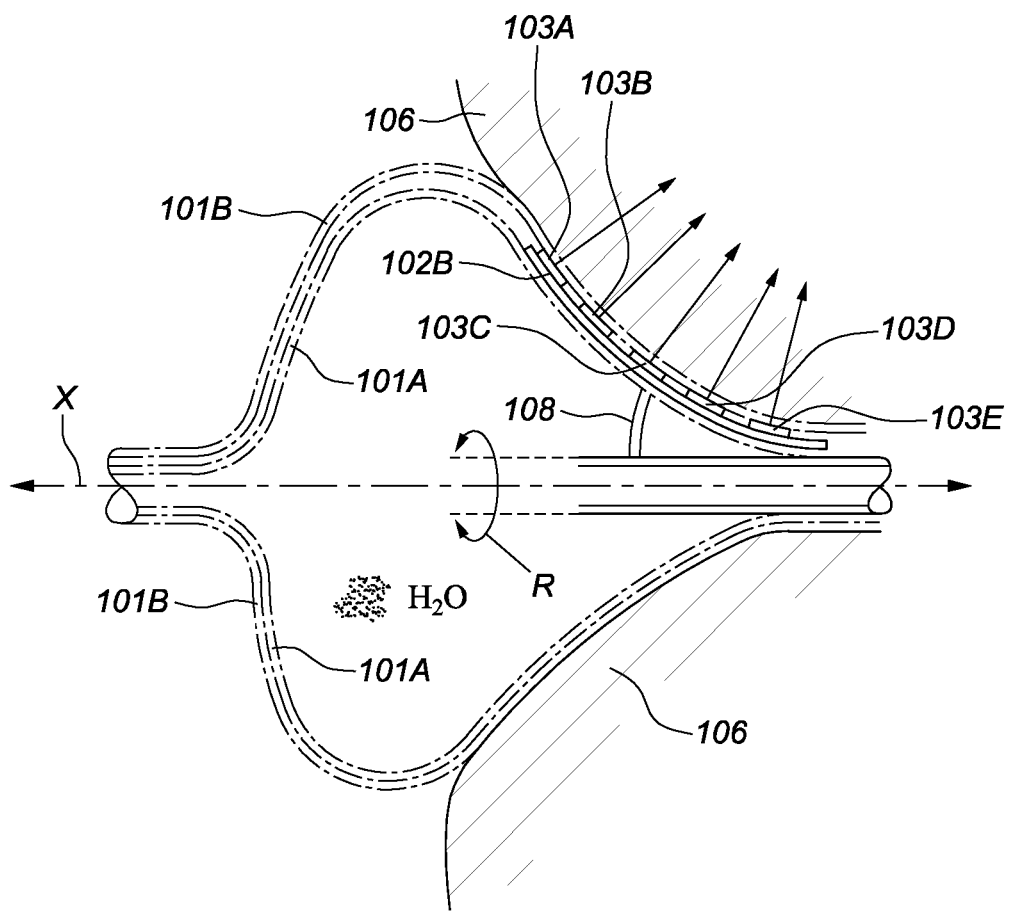
FIG. 7 is a schematic depiction of another embodiment of a PAR ablation device including two balloons.

FIG. 7 is a schematic depiction of another embodiment of a PAR ablation device involving two balloons, 101A and 101B. The second balloon, 101B, can be present between the fixed ablation elements 103A-103E and the antrum tissue 106. As further shown in FIG. 7, a spline 102B may be bendable (or remain flat like spline 102A in FIG. 6A). One or more splines 102B may be rotatable in a direction R about the catheter axis X.

Although at least one embodiment of a device for PAR ablation has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising:
   a catheter shaft having a proximal end portion, a distal end portion, and a distal tip portion, the catheter shaft defining a delivery lumen;
   a balloon forming the distal tip portion of the catheter shaft, the balloon defining a volume in fluid communication with the delivery lumen, the balloon including a balloon surface, a proximal end portion, and a distal end portion;
   a deformable spline configured to be rotated relative to a longitudinal axis of the catheter, the deformable spline extending over the balloon; and
   an ablation element coupled to the deformable spline, a location of the ablation element being dynamically adjustable along a length of the balloon surface from the proximal end portion of the balloon to the distal end portion of the balloon, wherein the ablation element is configured to form lesions in or near pulmonary vein antral tissue.

2. The catheter of claim 1, wherein the balloon is configured to position the ablation element adjacent to or against a target tissue.

3. The catheter of claim 1, wherein the balloon is configured to deform the spline.

4. The catheter of claim 3, wherein the ablation element is slidably coupled to the spline.

5. The catheter of claim 3, wherein the ablation element is mounted in a fixed position on the spline.

6. The catheter of claim 1, further comprising at least one of a position sensor, a temperature sensor, or a sensing electrode.

7. The catheter of claim 1, wherein the delivery lumen is configured to deliver irrigation fluid.

8. A catheter comprising:
   an elongate shaft structure comprising a proximal end and a distal end;
   wherein the distal end comprises a distal tip ablation region including an energy transfer balloon;
   wherein a surface of the energy transfer balloon comprises at least one conductive ablating region, the at least one conductive ablating region comprising a non-porous, grooved region of the surface of the energy transfer balloon; and
   wherein the energy transfer balloon further includes a non-ablating region, and wherein a thickness of the non-ablating region is greater than a thickness of the at least one conductive ablating region.

9. The catheter of claim 8, wherein the energy transfer balloon is configured to be positioned against a target tissue.

10. The catheter of claim 8, further comprising at least one of a position sensor, a temperature sensor, or a sensing electrode.

11. The catheter of claim 8, wherein the non-ablating region of the energy transfer balloon comprises a porous material.

* * * * *